United States Patent [19]

Ciccarelli et al.

[11] 4,263,510
[45] Apr. 21, 1981

[54] COMBINED X-RAY DIFFRACTION AND FLUORESCENCE SPECTROSCOPY APPARATUS WITH ENVIRONMENTALLY CONTROLLABLE CHAMBER

[75] Inventors: Michael F. Ciccarelli, Troy; Raymond P. Goehner, Clifton Park, both of N.Y.

[73] Assignee: General Electric Company, Schenectady, N.Y.

[21] Appl. No.: 62,218

[22] Filed: Jul. 30, 1979

[51] Int. Cl.³ ............................................. G01N 23/20
[52] U.S. Cl. .............................. 250/272; 250/277 CH
[58] Field of Search ............. 250/277 R, 277 CH, 272

[56] References Cited

U.S. PATENT DOCUMENTS 3,105,902  10/1963  Ostrofsky et al. ............ 250/277 CH

OTHER PUBLICATIONS

Jenkins, "Interdependence of X-ray Diffraction & X-ray Fluorescence Data", Advances in X-ray Analysis, vol. 21, pp. 7-21, C. Barrett et al. editors.
Ciccaralli et al., "A Diffractometer Based Energy Dispersive Elemental Analyser", Advances in X-ray Analysis, vol. 22, McCarthy et al. ed., pp. 251-253.
Kirk-Othmer, Encyclopedia of Chemical Technology, 2nd ed., vol. 22, 1968, pp. 438-467.

*Primary Examiner*—Alfred E. Smith
*Assistant Examiner*—Carolyn E. Field
*Attorney, Agent, or Firm*—Leo I. MaLossi; James C. Davis, Jr.

[57] ABSTRACT

The sensitivity of XRD-XRF apparatus for elements having atomic no. below 16 can be substantially increased by use of an environmentally controllable three-cylinder x-ray path chamber in combination with such apparatus. Use of the chamber has surprisingly been found to sufficiently increase the sensitivity so that element-identifying or characteristic lines of elements having atomic numbers at least as low as 10 can be measured by the improved XRD-XRF apparatus of this invention.

1 Claim, 4 Drawing Figures

COMBINED X-RAY DIFFRACTION AND FLUORESCENCE SPECTROSCOPY APPARATUS WITH ENVIRONMENTALLY CONTROLLABLE CHAMBER

BACKGROUND OF THE INVENTION

This invention relates to improvements in scanning x-ray apparatus capable of performing both x-ray diffraction and x-ray fluorescence spectroscopy.

Numerous x-ray apparatuses capable of performing both x-ray diffraction (XRD) and x-ray fluorescence (XRF) spectroscopy are well known in the x-ray art. For simplicity, apparatus of this type is referred to herein as "XRD-XRF" apparatus.

In general, XRD-XRF apparatus comprises (A) a gonimeter having a first rotatable platform and (B) means supported by the platform for holding the specimen in a position intersected by the axis of rotation of said first rotatable platform. Also included are (C) means for generating X-rays, (D) a source collimator for collimating the generated X-rays and beig so disposed that the collimated X-rays are incident on the specimen in the direction of the axis of said collimator, and (E) detecting means for detecting X-rays reflected from said specimen in response to incidence thereon of said collimated rays, said detecting means terminating at one end thereof in a snout for introducing the reflected X-rays into the detecting means.

Also included is (F) a wave-dispersive or energy-dispersive analyzer disposed near the entry end of said snout and operably associated with said detecting means for analyzing both X-ray fluorescent emission and absorption spectra and X-ray diffraction patterns generated by incidence of said collimated rays on said specimen.

Further included are, (G) first rotating means for rotating said specimen holder such that the specimen rotates relative to the incident X-rays (collimator axis) to a variable angular displacement in the plane containing the collimator axis and perpendicular to said axis of rotation, and (H) means operable in conjunction with such rotation of said specimen holder for concurrently rotating said detector such that said snout rotates relative to said collimator axis to a variable angular displacement $2\theta$ in said plane such that for each value of displacement $\theta$ the value of $2\theta$ displacement is substantially double that of displacement $\theta$.

An example of a well known x-ray apparatus encompassed by the above description is the XRD-6 Diffractometer introduced commercially by General Electric Company and now commercially available from the Diana Corporation (West Haven, Connecticut and Woburn, Massachusetts). The sales and technical brochures for the XRD-6 Diffractometer are incorporated herein by reference.

It has been heretofore known, in principle, that x-ray analysis and especially x-ray fluorescent spectrometry can be enhanced by employing a vacuum chamber for the x-ray path. See generally Kirk-Othmer, *Encyclopedia of Chemical Technology*, 2nd ed. (1968), vol. 22, pages 438–467 and the Jenkins article "Interdependence of X-Ray Diffraction and X-Ray Fluorescence Data" in *Advances in X-Ray Analysis*, edited by Barrett et al., vol. 21, pages 7–21. In FIG. 6 at page 20 of the referenced article, Jenkins shows a diagram of an energy dispersive spectrometer/diffractometer combination and states a disadvantage of that apparatus as "A disadvantage with this configuration is the difficulty in completely removing air from the path of the fluorescence emission and, as a result, only characteristic lines down to $S(Z=16)$ can be measured."

The prior art attempts to enhance the quality of x-ray analysis by incorporating x-ray path vacuum chambers into XRD-XRF apparatus of the Jenkins and other configurations have not been entirely satisfactory from the standpoint of measurability of characteristic lines of light elements, i.e. elements having atomic numbers (Z) below 16.

Briefly stated, it has unexpectedly now been found, by practice of the present invention, that the sensitivity of XRD-XRF apparatus for elements having atomic no. below 16 can be substantially increased by use of an environmentally controllable three-cylinder x-ray path chamber in combination with such apparatus. Use of the chamber (described in greater detail below) has surprisingly been found to sufficiently increase the sensitivity so that element-identifying or characteristic lines of elements having atomic numbers at lest as low as 10 can be measured by the improved XRD-XRF apparatus of this invention.

DESCRIPTION OF THE INVENTION

Generally stated, in one aspect of this invention, there is provided an improvement over the XRD-XRF apparatus described above. In the improvement, the XRD-XRF apparatus further comprises an environmentally controllable chamber for controlling the environment in which the specimen to be analyzed is held.

The chamber includes:

(a) a first hollow cylinder defining a cavity within which lies the specimen and the portion of said incident and reflected x-rays at least from the exit of the collimator and at least to the entrance of said snout, said first cylinder being disposed such that its central axis is both perpendicular to said collimator axis and coaxial with said axis of rotation, (b) a second hollow cylinder surrounding the outer periphery of said first cylinder, disposed closely adjacent thereto and mounted for relative angular displacement therebetween, (c) a third hollow cylinder surrounding the outer periphery of said second cylinder and disposed closely adjacent thereto and mounted for relative angular displacement therebetween, each of said first, second and third cylinders being disposed coaxially of said rotation axis and coaxially of each other, the axis of each cylinder extending perpendicular to the direction of the axis of said source collimator, (d) means for air-tight sealing of mutually opposite ends of said cavity, said first cylinder having both (i) a hole extending through the wall thereof, said hole being shaped substantially in the shape of a transverse section of said collimator and bordered by a closed surface of the wall for peripherally engaging said collimator, and (ii) a first slot extending radially through said wall and peripherally therealong, the peripheral extent of said first slot being of an angle equal in value to the angle through which said detector is operably movable, a portion of said first slot being disposed approximately diametrically from said first hole, (e) means securing said second cylinder to said first platform such that said second cylinder rotates as an integral unit with said specimen holder, (f) said third cylinder having both (i) a second hole extending through the wall thereof, said hole being shaped substantially in the shape of a transverse section of said snout and bordered by a closed surface of said last-mentioned wall for peripherally engaging said snout and (ii) a second slot extending radially through said last-mentioned wall and peripherally therealong, the peripheral extent of said second slot being equal in angular value to the peripheral extent of said first slot, (g) said second cylinder having third and fourth circumferentially spaced-apart slots extending radially through the wall thereof and peripherally therealong, the peripheral extent of each of said third and fourth slots being of an angle substantially equal in value to half the angle through which said detector is operably movable, said third slot being radially and peripherally aligned with a portion of said first slot, a trailing end of said third slot being radially aligned with said one end portion of said first slot and with said second hold when said snout is in said first position and $\theta$ is substantially 0°, whereby said snout can extend through said second hole and said first and third slots, a leading end of said third slot being radially aligned with said second hole and with the other end of said first slot when said second cylinder and said snout are rotated to a second position wherein said snout is angularly displaced from said first position by the maximum angular amount permitted by said first slot, said fourth slot being radially and peripherally aligned with a portion of said second slot, a leading end of said fourth slot being radially aligned with said first hole and with said leading end of said second slot when said snout is in said first position and $\theta$ is substantially zero degrees, whereby said collimator can extend through said first hole and said second and fourth slots, (h) means for placing said cavity in flow communication with a source of inert gas or with a vacuum drawing source such that said cavity can be substantially filled with said inert gas or be substantially evacuated to environmentally control the X-ray path, (i) means for gas tightly sealing each of said cylinders to its adjacent cylinder or cylinders, and (j) means for rotating said third cylinder relative to said axis of rotation such that said third cylinder rotates as an integral unit with said snout.

BRIEF DESCRIPTION OF THE DRAWING

This invention will be more fully understood by referring to the following detailed description taken with the accompanying drawing, which illustrates the best mode contemplated for carrying out the invention. In the drawing, wherein like numeals refer to similar elements throughout.

DETAILED DESCRIPTION OF THE INVENTION AND OF THE MANNER AND PROCESS OF MAKING AND USING IT

Figure 1:
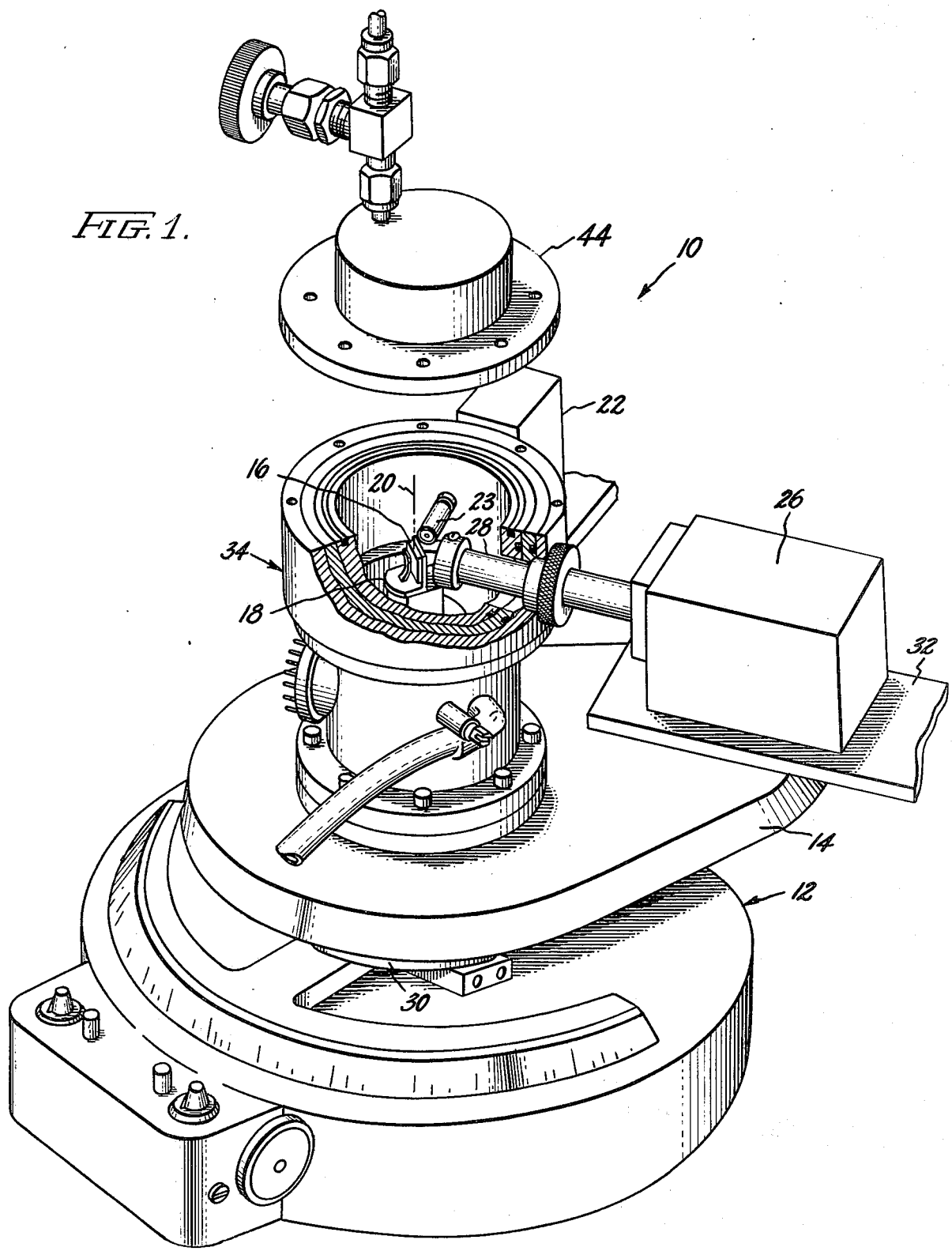
FIG. 1 is a fragmentary perspective view embodying this invention and illustrating an improved XRD-XRF apparatus including an environmentally controllable specimen chamber as a component thereof.
Figure 4:
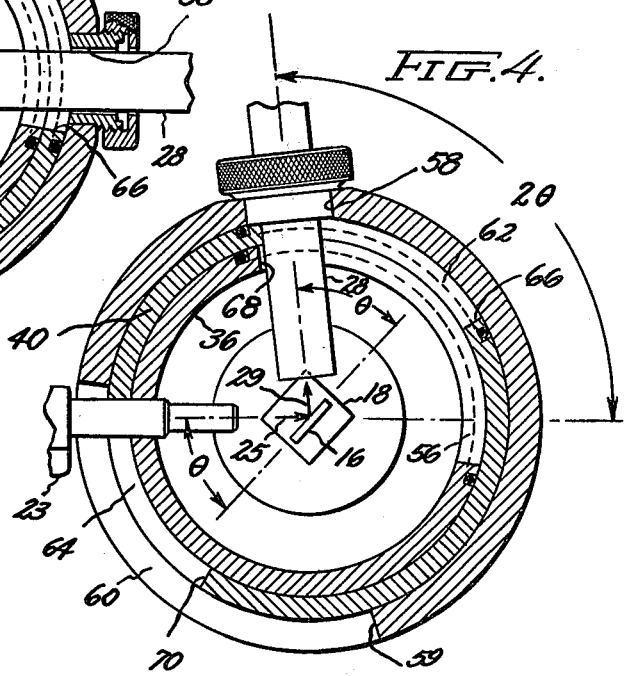
FIG. 4 is a schematic illustration of the relative angular displacement of various components of the improved apparatus.

Referring now to the drawing, especially to FIG. 1, there is shown improved XRD-XRF apparatus 10 including first goniometer 12 having a first rotatable platform 14 for indirectly supporting specimen 16 and holding assembly 18 supported by the platform for holding the specimen in a position intersected by the axis of rotation 20 of the platform. Means for generating X-rays is provided by X-ray tube 22 supported by means not shown. Source collimator 23 is included for collimating the generated X-rays and so disposed that the collimated X-rays indicated by arrow 25 (FIG. 4) are incident on the specimen in the direction of axis 24 of the collimator. Detector 26 is included for detecting X-rays reflected from the specimen in response to incidence thereon of the collimated rays. The detector terminates at one end thereof in snout 28 for introducing the reflected X-rays indicated by arrow 29 (FIG. 4) into the detector. Wave-dispersive or energy-dispersive analyzer (not shown) is disposed near the entry end of (and within) the snout. The analyzer is operably associated with the detector for analyzing both X-ray fluorescent emission and absorption spectra and X-ray diffraction patterns generated by incidence of the collimated rays on the specimen.

A rotational drive 30 is provided for rotating the platform and specimen holder 18 secured thereto such that the holder and therein-held specimen reversibly rotate relative to the incident X-rays (collimator axis) to a variable angular displacement $\theta$ in the plane containing the collimator axis and perpendicular to the axis of rotation. A drive (not shown) operable in conjunction with such rotation of the specimen holder is operably connected to detector platform 32 for rotating the detector concurrently with rotation of the specimen and its holder such that the snout rotates relative to the collimator axis to a variable angular displacement $2\theta$ in the above-stated plane such that for each value of displacement $\theta$ the value of the $2\theta$ displacement is substantially double that of the displacement $\theta$.

In accordance with the present invention, the XRD-XRF apparatus (which preferably includes an XRD-6 diffractometer) further comprises, in combination with the above, environmentally controllable chamber 34 for controlling the environment in which the specimen is held. The chamber comprises a first or inner hollow cylinder 36 defining cavity 38 within which lies the specimen and at least the portion of the incident and reflected x-rays extending from the exit of the collimator and to the entrance of the snout. The first cylinder is disposed such that its central axis is both perpendicular to the collimator axis 24 and coaxial with the axis 20 of rotation. A second or intermediate hollow cylinder 40 surrounds the outer periphery of the inner cylinder and is disposed closely adjacent thereto and mounted for relative angular displacement therebetween. A third or outer hollow cylinder 42 surrounds the outer periphery of the second cylinder and is disposed closely adjacent thereto and mounted for relative angular displacement therebetween. Each of the first, second and third cylinders is disposed coaxially of the rotation axis 20 and coaxially of each other. The axis of each cylinder extends perpendicular to the direction of the axis of the source collimator.

Figure 2:
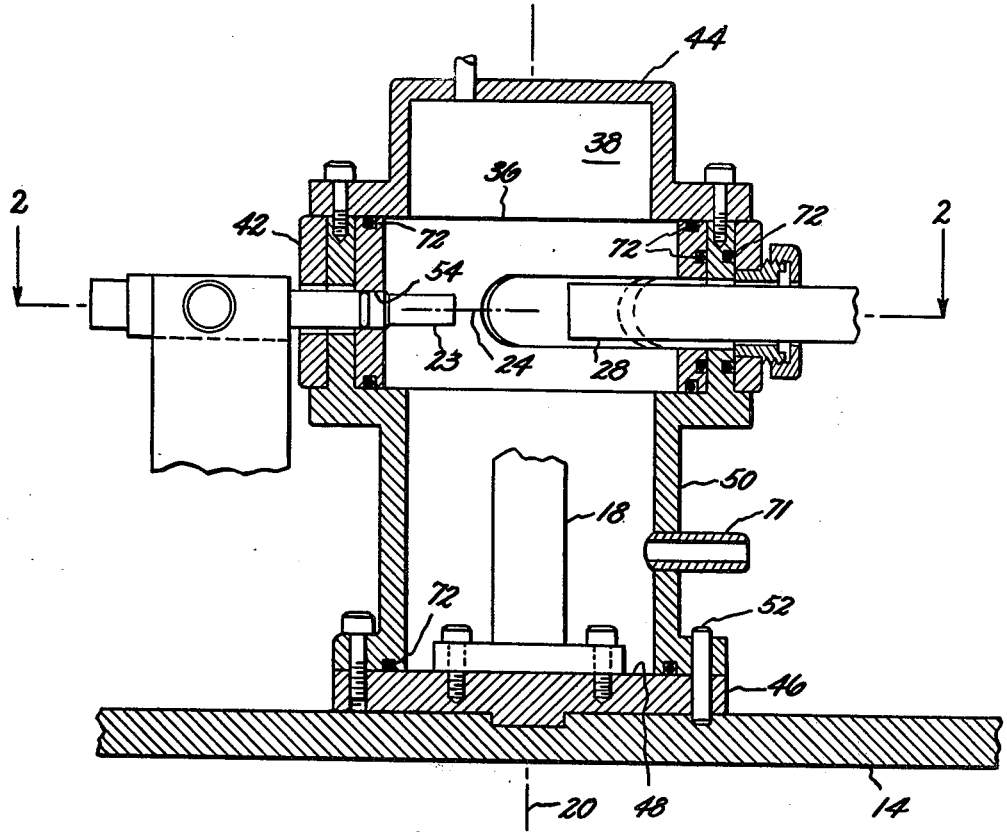
FIG. 2 is a fragmentary elevation view, partly in section, of the improved XRD-XRF apparatus.

Air-tight sealing of mutually opposite ends of the cavity is provided, e.g. as shown in FIG. 2, at one end by cover 44 in such sealing engagement with annular ends of the cylinders and at the other end plate 46, which is secured in such sealing engagement with annular face 48 provided in extension 50 of the intermediate cylinder. The chamber is secured to platform 14 by securing means illustrated by fastener 52. The inner cylinder also has a first slot 56 extending radially through its wall and peripherally therealong. The peripheral or circumferential extent of the first slot is of an angle slightly more than equal in value to the angle through which the detector (and its snout) is operably movable, e.g. up to 95° or more. One end portion of the first slot is disposed approximately diametrically of the cavity from the first hole when the snout is in a first position wherein the snout is approximately coaxially aligned with the collimator and $\theta$ is substantially 0°. The angle $\theta$ is the angle of incidence of the collimated x-rays on the specimen.

As a result of securing the intermediate or second cylinder to the platform 14, this cylinder is rotatable as an integral unit with the specimen holder.

Figure 3:
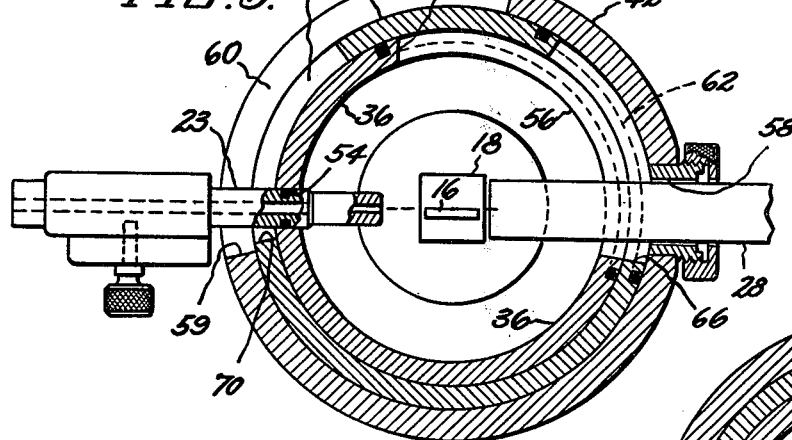
FIG. 3 is a sectional view taken on line 2—2 of FIG. 2.

The outer or third cylinder has a second hole 58 extending through the wall thereof and being shaped substantially in the shape of a transverse section of the snout 28 and bordered by a closed surface of the last-mentioned wall for engaging the snout peripherally thereabout. The outer cylinder also has a second slot 60 extending radially through its wall and peripherally therealong for accomodating the collimator. The peripheral extent of the second slot is substantially equal in angular value to the peripheral extent of the first slot 56. One end portion (the leading end portion 59 during periods of increasing $\theta$) of the second slot 60 is disposed in radial alignment with the first hole 54 when $\theta$ is substantially zero degrees and the snout is in the first position set forth below (which position is shown in FIG. 3).

The second or intermediate cylinder has third and fourth circumferentially spaced-apart slots 62 and 64, respectively, each extending radially through the wall thereof and peripherally therealong. The peripheral extent of each of the latter two slots is of an angle substantially equal in value to half the angle through which the detector is operably movable. The third slot 62 is radially and peripherally aligned with a portion of the first slot 56. A trailing end 66 (i.e. trailing during increasing $\theta$) of the third slot is radially aligned with the aforementioned one end 59 of the first slot 56 and with the second hole when the snout is in the aforesaid first position and $\theta$ is substantially 0° (FIG. 3), whereby the snout extends through the second hole 58, the first slot 56 and the third slot 62. A leading end of the third slot 60 is radially aligned with the second hole 58 and with the other end 68 of the first slot when the second cylinder and the snout are rotated to a second position (shown in FIG. 4), wherein the snout is angularly displaced from the first position by the maximum angular amount permitted by the first slot.

The fourth slot 64 is radially and peripherally aligned with a portion of the second slot 60. The leading end 70 of the fourth slot is radially aligned with the first hole 54 and with the leading end 59 of the second slot when the snout is in the first position and $\theta$ is substantially zero degrees, whereby said collimator extends through the first hole, the second slot 60 and the fourth slot 64.

Pipe 71 received in a hole in the extension of the intermediate cylinder is provided for placing the cavity in flow communication with a source of inert gas or with a vacuum-drawing source such that the cavity can be substantially filled with the inert gas or be substantially evacuated, whereby the X-ray path is environmentally controlled.

Also included are means (e.g. a plurality O-rings 72 held in recesses of the surfaces of the cylinders) for gas-tightly sealing each of the cylinders to its adjacent cylinder or cylinders, and a drive (not shown) for rotating said third cylinder relative to the axis of rotation such that the third cylinder rotates as an integral unit with the snout.

Best Mode Contemplated

The best mode contemplated for carrying out the invention has been set forth above in connection with the detailed description given with reference to the illustrated best mode. In the best mode, nylon O-ring seals and brass is employed for the chamber walls.

It is understood that the foregoing detailed description is given merely by way of illustration and that many variations may be made therein without departing from the spirit or scope of this invention.

What is claimed is:

1. In a scanning X-ray apparatus capable of performing both X-ray diffraction and X-ray fluorescence spectroscopy on a specimen said apparatus comprising:
   (A) a goniometer having a first rotatable platform
   (B) means supported by the platform for holding the specimen in a position intersected by the axis of rotation of said first rotatable platform,
   (C) means for generating X-rays,
   (D) a source collimator for collimating the generated X-rays and being so disposed that the collimated X-rays are incident on the specimen in the direction of the axis of said collimator,
   (E) detecting means for detecting X-rays reflected from said specimen in response to incidence thereon of said collimated rays, said detecting means terminating at one end thereof in a snout for introducing the reflected X-rays into the detecting means.
   (F) a wave-dispersive or energy-dispersive analyzer disposed near the entry end of said snout and operably associated with said detecting means for analyzing both X-ray fluorescent emission and absorption spectra and X-ray diffraction patterns generated by incidence of said collimated rays on
   (G) said specimen, first rotating means for rotating said specimen holder such that the specimen rotates relative to the incident X-rays (collimator axis) to a variable angular displacement in the plane containing the collimator axis and perpendicular to said axis of rotation,
   (H) means operable in conjunction with such rotation of said specimen holder for concurrently rotating said detector such that said snout rotates relative to said collimator axis to a variable angular displacement $2\theta$ in said plane such that for each value of displacement $\theta$ the value of the $2\theta$ displacement is substantially double that of this displacement $\theta$, the improvement wherein said apparatus further comprises in combination with the above, an environmentally controllable chamber for concontrolling the environment in which the specimen is held, said chamber comprising:

(a) a first hollow cylinder defining a cavity within which lies the specimen and the portion of said incident and reflected x-rays at least from the exit of the collimator and at least to the entrance of said snout, said first cylinder being disposed such that its central axis is both perpendicular to said collimator axis and coaxial with said axis of rotation, (b) a second hollow cylinder surrounding the outer periphery of said first cylinder, disposed closely adjacent thereto and mounted for relative angular displacement therebetween, (c) a third hollow cylinder surrounding the outer periphery of said second cylinder and disposed closely adjacent thereto and mounted for relative angular displacement therebetween, each of said first, second and third cylinders being disposed coaxially of said rotation axis and coaxially of each other, the axis of each cylinder extending perpendicular to the direction of the axis of said source collimator.

(d) means for air-tight sealing of mutually opposite ends of said cavity, said first cylinder having both (i) a hole extending through the wall thereof, said hole being shaped substantially in the shape of a transverse section of said collimator and bordered by a closed surface of the wall for peripherally engaging said collimator, and (ii) a first slot extending radially through said wall and peripherally therealong, the peripheral extent of said first slot being of an angle equal in value to the angle through which said detector is operably movable, one end portion of said first slot being disposed approximately diametrically from said first hole when said snout is in a first position wherein said snout is approximately coaxially aligned with said collimator and $\theta$ is substantially 0°, said $\theta$ also being the angle of incidence of the collimated x-rays on said specimen, (e) means securing said second cylinder to said first platform such that said second cylinder rotates as an integral unit with said specimen holder, (f) said third cylinder having both (i) a second hole extending through the wall thereof, said hole being shaped substantially in the shape of a transverse section of said snout and bordered by a closed surface of said last-mentioned wall for peripherally engaging said snout and (ii) a second slot extending radially through said last-mentioned wall and peripherally therealong, the peripheral extent of said second slot being equal in angular value to the peripheral extent of said first slot, one end portion (the heading end portion) of said second slot being disposed in radial alignment with said first hole when $\theta$ is substantially zero degrees and said snout is in the first position set forth below, (g) said second cylinder having third and fourth circumferentially spaced-apart slots extending radially through the wall thereof and peripherally therealong, the peripheral extent of each of said third and fourth slots being of an angle substantially equal in value to half the angle through which said detector is operably movable, said third slot being radially and peripherally aligned with a portion of said first slot, a trailing end of said third slot being radially aligned with said one end portion of said first slot and with said second hole when said snout is in said first position and $\theta$ is substantially 0°, whereby said snout can extend through said second hole and said first and third slots, a leading end of said third slot being radially aligned with said second hole and with the other end of said first slot when said second cylinder and said snout are rotated to a second position wherein said snout is angularly displaced from said first position by the maximum angular amount permitted by said first slot, said fourth slot being radially and peripherally aligned with a portion of said second slot, a leading end of said fourth slot being radially aligned with said first hole and with said leading end of said second slot when said snout is in said first position and $\theta$ is substantially zero degrees, whereby said collimator can extend through said first hole and said second and fourth slots, (h) means for placing said cavity in flow communication with a source of inert gas or with a vacuum drawing source such that said cavity can be substantially filled with said inert gas or be substantially evacuated to environmentally control the X-ray path, (i) means for gas tightly sealing each of said cylinders to its adjacent cylinder or cylinders, and means for rotating said third cylinder relative to said axis of rotation such that said third cylinder rotates as an integral unit with said snout.

* * * * *